US007525013B2

(12) United States Patent
Hildebrand et al.

(10) Patent No.: US 7,525,013 B2
(45) Date of Patent: Apr. 28, 2009

(54) SOYBEAN SELECTION SYSTEM BASED ON AEC-RESISTANCE

(75) Inventors: David Hildebrand, Lexington, KY (US); Suryadevara S. Rao, Lexington, KY (US)

(73) Assignee: United Soybean Board, St. Louis, MO (US)

(*) Notice: Subject to any disclaimer, the term of this patent is extended or adjusted under 35 U.S.C. 154(b) by 185 days.

(21) Appl. No.: 10/562,225

(22) PCT Filed: Jun. 23, 2004

(86) PCT No.: PCT/US2004/020039

§ 371 (c)(1),
(2), (4) Date: Dec. 23, 2005

(87) PCT Pub. No.: WO2005/017108

PCT Pub. Date: Feb. 24, 2005

(65) Prior Publication Data

US 2006/0117413 A1 Jun. 1, 2006

Related U.S. Application Data

(60) Provisional application No. 60/483,103, filed on Jun. 30, 2003.

(51) Int. Cl.
*C12N 15/82* (2006.01)
(52) U.S. Cl. ..................................................... 800/278
(58) Field of Classification Search ....................... None
See application file for complete search history.

(56) References Cited

U.S. PATENT DOCUMENTS

| | | | |
|---|---|---|---|
| 5,084,082 A | 1/1992 | Sebastian | |
| 5,367,110 A | 11/1994 | Calili et al. | |
| 5,378,825 A | 1/1995 | Cook et al. | |
| 5,773,691 A * | 6/1998 | Falco et al. | 800/287 |
| 5,935,835 A | 8/1999 | Marshall et al. | |
| 6,093,568 A | 7/2000 | Davies et al. | |
| 6,342,658 B1 | 1/2002 | DeBonte et al. | |
| 6,495,738 B1 | 12/2002 | Folkerts et al. | |
| 6,552,250 B1 | 4/2003 | Nykiforuk et al. | |
| 2003/0024014 A1 | 1/2003 | Cheng et al. | |
| 2003/0061633 A1* | 3/2003 | Vorst et al. | 800/278 |

OTHER PUBLICATIONS

Maughan et al 1999, In Vitro Cell. Dev. Biol.—Plant, 35: 344-349.*
Silk et al 1997, Plant Molecular Biology 33: 931-933.*
Maughan et al., "In Vitro Cell", Dev. Biol.-Plant, Jul.-Aug. 1999, vol. 35, pp. 344-349.
Silk et al., "Plant Molecular Biology", 1994, vol. 26, pp. 989-993.
"Soybean Somatic Embryogenesis and Trasformation", 3 pages, dated Jun. 10, 2004, http://www/cropsoil.uga.edu/soy-engineering/soytransformation.html.
"Soybean Transformation", 7 pages, downloaded May 16, 2005 http://www2.oardc.ohio-state.edu/plantranslab/d20.htm.
Zhanyuan Zhang, "Transformation of Recalcitrant Crop Species: A Case Study on Agrobacterium-Mediated Transfromation of Soybean and its Implication to Maise Transformation", Plant Transformation Core Facility, 1 page, dated Jan. 13-17, 2001 http://www/intl-pag.org/9/abstracts/W38_05.html.
McAlvin et al., "Transgenic Expression of the Soybean Apyrase in Lotus Japonicus Enhances Nodulation1", Plant Physiology, Apr. 2005, vol. 137, p. 1456-1462.
Jaiwal et al., "Strategies to Deal With the Convern About Marker Genes in Transgenic Plants: Some Environment-Friendly Approaches", Current Science, vol. 83, No. 2, Jul. 25, 2002, pp. 128-136.
Morten Joersbo, "Advances in the Selection of Transgenic Plants Using Non-Antibiotic Marker Genes", Physiologia Plantarum, vol. 111, 2001, pp. 269-272.
Miki et al., "Selectable Marker Genes in Transgenic Plants: Applications, Alternatives and Biosafety", Journal of Biotechnology, vol. 107, 2004, pp. 193-232.
Suryadevara S. Rao et al., "Lysine-Threonine and Lysine-Analog S-(2-Aminoethyl)-L-cysteine as Alternative Non-antiobiotic selection System for Soybean somatic Embyros", 1 Page , presented at Conference in Barcelona, Spain, during Jun. 23-28, 2003.
Arnold, L.D., R.G. May and J.C. Vederas. 1988. Synthesis of optically pure α-amino acids via salts of α-amino-β-propiolactone. J. Am. Chem. Soc. 110: 2237-2241.
Boy, E., Borne, F. and Patte, J.C. (1979). Isolation and identification of mutants constitutive for aspartate kinase III synthesis in *Escherichia coli* K12. Biochemie 61: 1151-1160.
Bright, S.W.J. and P.R. Shewry. 1983. Improvement of protein quality in cereals. CRC Crit. Rev. Plant Sci. 1: 49-93.
Cohen, C.N. and I Saint-Girons. 1987. Biosynthesis of threonine, lysine and methionine. In: F.C. Neidhardt, ed., *Escheichia coli* and *Salmonella typhimurium*: Cellular and Molecular Biology. Amer. Soc. Microbiol., Washington, D.C. pp. 429-444.

(Continued)

*Primary Examiner*—David H Kruse
(74) *Attorney, Agent, or Firm*—Venable LLP; Michael A. Gollin; Thomas F. Barry (57) ABSTRACT

A method for generating a transgenic soybean plant comprising in its genome a heterologous nucleic acid sequence of interest, comprises introducing into a soybean somatic embryo a polynucleotide encoding a functional dihydrodipicolinate synthase (DHPS) polypeptide, and a polynucleotide encoding a heterologous polypeptide of interest, operably linked to expression control sequences, wherein DHPS expressed from the introduced DHPS-encoding polynucleotide is effective to render the embryo resistant to S-2-aminoethylcysteine (2-AEC), and contacting the embryo with 2-AEC, under conditions effective for an embryo which expresses the DHPS to grow selectably and mature into a soybean plant that expresses a desired trait, and preferably includes no antibiotic resistance marker sequence.

32 Claims, 4 Drawing Sheets

OTHER PUBLICATIONS

Ghislain, M., V. Frankard and M. Jacobs. 1995. A dinucleotide mutation in dihydrodipicolinate synthase of Nicotiana sylvestris leads to lysine overproduction. The Plant J. 8: 733-743.

Jacobs, M., Negrutiu, I., Dirks, R. and Cammaerts, D. (1987). Selection programs for isolation and analysis of mutants in plant cell cultures. In: Green C.E., Somers D.A., Hackett W.P. Biesboer DD (eds) Plant Biology. vol. 3: plant tissue and cell culture. Alan R. Liss, New York pp. 243-264.

Perl A, Galili S, Shaul O, Ben-Tzvi I, Galili G (1993) Bacterial dihydrodipicolinate synthase and desensitized aspartate kinase: Two novel selectable markers for plant transformation. Bio Tech 11: 715-727.

Matsumoto, N. 1984. Isolation and identification of S-2-aminoethyl-L-systeine from Rozites caperta and 2-amino-3-butenoic acid from Rhodophyllus crassipes and their antibacterial activity. Toho Igakkai Zasshi 31: 249-264.

Negrutiu, I., A. Cattoir-Reynearts, I. Verbruggen and M. Jacobs, 1984. Lysine overproducer mutants with an altered dihydrodipicolinate synthase from protoplast culture of Nicotiana sylvestris (Spegazzini and Comes). Theor. Appl. Genet. 68: 11-20.

Shaul, O. and Galili, G. (1992). Threonine overproduction in transgenic tobacco plants expressing a mutant desensitized aspartate kinase of *Escherichia coli*. Plant Physiology 100: 1157-1163.

Vauterin, M., V. Frankard and M. Jacobs. 2000. Functional rescue of a bacterial dapA auxotroph with a plant cDNA library selects for mutant clones encoding a feedback-insensitive dihydrodipicolinate synthase. The Plant J. 21: 239-248.

Falco SC, et al., Transgenic canola and soybean seeds with increased lysine, Biotechnology (NY) 13(6):577-82, 1995.

Shaul O, et al., Concerted regulation of lysine and threonine synthesis in tobacco plants expressing bacterial feedback-insensitive aspartate kinase and dihydrodipicolinate synthase, Plant Mol Biol;23(4):759-68, 1993.

Brinch-Pedersen H, et al., Plant Mol Biol; 32(4):611-20, 1996.

Karlin et al., (1993) Proc. Natl. Acad. Sci. USA 90:5873-5877.

Altschul et al. (1997) Nucleic Acids Res. 25:3389-3402.

Devereaux et al. (1984) Nucleic Acids Res. 12 (1):387-395.

Silk G.W. and B.F. Matthews, 1997, Plant molecular biology, 33:931-933.

Cremer J, Treptow C, Eggeling L, Sahm H., Regulation of enzymes of lysine biosynthesis in Corynebacterium glutamicum, J Gen Microbiol. Dec. 1988; 134 (Pt 12):3221-9.

Bonnassie S, Oreglia J, Sicard AM. Nucleic Acids Res. Nov. 11, 1990;18(21):6421.

Laber B, Gomis-Ruth FX, Romao MJ, Huber R, *Escherichia coli* dihydrodipicolinate synthase. Identification of the active site and crystallization, Biochem J. Dec. 1, 1992;288 (Pt 2):691-5.

Trick, H.N., R.D. Dinkins, E.R. Santarem, R. Di, V.M. Samoylov, C. Meurer, D. Walker, W.A. Parrott, J.J. Finer, and G.B. Collins. 1997. Recent advances in soybean transformation. Plant Tissue Culture and Biotechnology 3:9-26.

Hazel, C.B., T.M. Klein, M. Anis, H.D. Wilde, and W.A. Parrot. 1998. Growth characteristics and transformability of soybean embryogenic cultures. Plant Cell Reports 17:765-772.

Samoylov, V.M., D.M. Tucker, and W.A. Parrott. 1998. A liquid medium-based protocol for rapid regeneration from embryogenic soybean cultures. Plant Cell Reports 18:49-54.

Finer, J.J., and McMullen MD 1991. Transformation of soybean via particle bombardment of embryogenic suspension culture tissue. In Vitro Cellular & Developmental Biology. Plant 27:175-82.

Shaver, J., Bittel, D., Sellner, J., Frisch, D., Somers, D., Gengenbach, B. 1996 Single-amino acid substitutions elminate lysine inhibition of maize dihydrodipicolinate synthase. Proc. Natl Acad. Sci. USA, 93, 1962-1966.

International Search Report issued in PCT Application No. PCT/US2004/020039, mailed on Feb. 15, 2005.

Written Opinion issued in PCT Application No. PCt/US2004/020039, mailed on Feb. 15, 2005.

\* cited by examiner

| Figure 6a | Figure 6b |
|---|---|
| Liquid Media Protocol | Solid Media Protocol |
| D40 (Somatic embryo induction) (1.5 months) | D40 ( 1.5 months ) |
| D20 (Proliferation of Somatic Embryos) (1 month) | D20 ( 3 months ) |
| FN Suspension medium (Embryogenic culture establishment) (3 months) | Bombardment |
| | D20 ( 1 month ) |
| | D20 + selective agents ( 3-4 months ) |
| Bombardment | MSM6Ac (Maltose 6% + Activated Charcoal) (Remove 2,4-D) ( 1 month ) |
| FL Suspension medium (without selective agents) (2-3 months) | |
| Recovery of Transformants | MSM6 (Maturation) (1 month ) |
| FL-Superlite (Maturation) (3 weeks) | Desiccation ( 4-5 days ) |
| Desiccation (4-5 days ) | Germination ( 1 month ) |
| MSO3 ( 3% sucrose) Germination medium without hormones (1 month) | Regeneration ( 1-2 months ) |
| Regeneration (1-2 months) | Seeds ( 2 months ) |
| Seeds (2 months) | |

SOYBEAN SELECTION SYSTEM BASED ON AEC-RESISTANCE

CROSS REFERENCE TO RELATED APPLICATIONS

This application claims the benefit of International Application No. PCT/US2004/020039, International filing date Jun. 23, 2004, which claims the benefit of U.S. Provisional Patent Application Ser. No. 60/483,103, filed on Jun. 30, 2003, the disclosures of which are incorporated herein by reference.

FIELD OF THE INVENTION

The invention relates to methods of producing a transgenic soybean plant with improved qualities by introducing a dihydrodipicolinate synthase (DHPS) gene conferring S-2-aminoethyl-cysteine (AEC) resistance in soybean somatic embryos as a non-antibiotic selectable marker system. The resulting improved soybean plants eliminate concerns associated with antibiotic resistance genes, and because they are AEC tolerant, they are suitable for agricultural use with AEC as an herbicide.

BACKGROUND OF THE INVENTION

Because soybeans are a good source of oil, isoflavones and proteins, genetic engineering of soybeans for higher value cultivars has tremendous market value. Soybean transformation procedures include gene gun bombardment of somatic embryos. The bombarded embryos are selected with a selectable marker that is part of the introduced DNA. For soybean somatic embryo selection, the antibiotic hygromycin is often used. Market forces and health and safety concerns have created a need to eliminate such genes from improved crop varieties, but existing processes are time consuming. There is a need for non-antibiotic selection maker genes that can eliminate these problems. Only a limited number of non-antibiotic resistance markers are available for plant improvement. For example, herbicide selection systems like glyphosate may be useful but are generally not available for use.

Soybean cellular selection systems are exceptional in that they are recalcitrant to selection that commonly works with many plant cellular selection systems. For example, the most common cellular selection system for plant systems is kanamycin resistance conferred by an nptII gene, but after numerous failed attempts it was concluded that this selection system cannot be accomplished with soybeans. Antibiotic resistance markers have been used in seeds to produce transgenic canola, tobacco, barley, and soybean plants that express a bacterial variant of DHPS that is insensitive to AEC. The presence of antibiotic resistance genes in these plants is an undesirable result.

AEC is a lysine analog that naturally occurs in the mushroom *Rozites caperta* (Matsumoto, 1984; Cadogan et al., 1996). It also can be synthesized using N-(tert-butoxycarbonyl)serine and ethanolamine (Arnold et al., 1988). AEC is an inhibitor of dihydrodipicolinate synthase (DHPS or DHDPS) killing cells and tissues due to an inability to synthesize lysine (Perl et al., 1993; Ghislain et al., 1995; Vauterin et al., 2000). AEC also inhibits AK and lysine is another inhibitor of DHPS (Negrutiu et al., 1984). It is known that the DHPS enzyme of *E. coli* is 50 fold less sensitive to AEC than plant enzymes (IC50 for lysine of 400 μmM–1 mM compared to 10 μM for plants.) (Jacobs et al., 2000)

SUMMARY OF THE INVENTION

The invention provides a method for making a transgenic soybean plant having no antibiotic resistance gene and improved soybean characteristics by selecting soybean somatic embryos with S-2-aminoethyl-cysteine (AEC or 2-AEC).

This invention relates, e.g., to a method for generating a transgenic soybean plant which comprises in its genome a heterologous nucleic acid sequence of interest, comprising:

introducing into a soybean somatic embryo a polynucleotide encoding a functional dihydrodipicolinate synthase (DHPS) polypeptide, operably linked to a first expression control sequence, and optionally a polynucleotide encoding a heterologous polypeptide of interest, operably linked to a second expression control sequence, wherein the first and second polynucleotides and expression control sequences may be the same or different, wherein DHPS expressed from the introduced DHPS-encoding polynucleotide is effective to render the embryo resistant to S-2-aminoethylcysteine, and contacting the embryo produced in (a) with 2-AEC, under conditions effective to allow an embryo which expresses the DHPS to grow selectably and to mature into a soybean plant, while inhibiting growth of non-transformed embryo cells.

Progeny of a transgenic soybean plant of the invention include seeds (beans) produced by the plant, as well as variants of the original plant which are produced by further genetic manipulations or crosses. For example, a transgenic soybean plant of the invention may be heterozygous for the DHPS or the heterologous polypeptide of interest; progeny of this plant include plants resulting from genetic manipulations which are homozygous for one of both of those genes.

The invention also relates to a method for generating a herbicide-resistant transgenic soybean plant comprising: introducing into a soybean somatic embryogenic culture a polynucleotide encoding a functional dihydrodipicolinate synthase (DHPS) polypeptide, operably linked to an expression control sequence, wherein DHPS expressed from the introduced DHPS-encoding polynucleotide is effective to render an embryo resistant to selection-effective amounts of S-2-aminoethylcysteine (2-AEC), and to render the plant resistant to herbicide-effective amounts of AEC, and contacting the embryo with selection effective amounts of 2-AEC.

The invention also relates to a herbicide-resistant transgenic soybean plant, or progeny thereof, comprising a polynucleotide encoding a functional dihydrodipicolinate synthase (DHPS) polypeptide, operably linked to an expression control sequence, wherein DHPS expressed from the introduced DHPS-encoding polynucleotide is effective to render the soybean plant resistant to herbicide-effective amounts of AEC, the plant having no antibiotic resistance marker.

The invention relates to a transgenic soybean plant comprising a polynucleotide encoding an AEC resistant DHPS that is expressible in soybean somatic embryos and a polynucleotide encoding a protein imparting a desired trait in the soybean plant or soybean, the plant being free of a polynucleotide encoding a polypeptide imparting antibiotic resistance.

DETAILED DESCRIPTION OF THE INVENTION

In describing preferred embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The embodiments of the invention may be modified or varied, and elements added or omitted, without departing from the invention, as appreciated by those skilled in the art in light of the above teachings. Each reference cited here is incorporated by reference as if each were individually incorporated by reference.

As used herein, the term polynucleotide is interchangeable with the terms oligonucleotide, oligomer, and nucleic acid. A polynucleotide of the invention may be a recombinant polynucleotide, a natural polynucleotide, or a synthetic or semi-synthetic polynucleotide, or combinations thereof. Polynucleotides of the invention may be RNA, PNA, LNA, or DNA, or combinations thereof. The nucleotides of a polynucleotide of the invention can be joined via various known linkages, e.g., ester, sulfamate, sulfamide, phosphorothioate, phosphoramidate, methylphosphonate, carbamate, etc., depending on the desired purpose, e.g., improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

A "functional dihydrodipicolinate synthase (DHPS) polypeptide" exhibits a detectable amount of at least one desirable function or property of a DHPS, such as those having SEQ ID NO: 3 or SEQ ID NO: 4. For example, the expression of the polypeptide renders the organism in which it is expressed (e.g., an *E. coli* bacterium or a soybean somatic embryo or a soybean plant or bean) resistant to growth inhibition by S-2-aminoethylcysteine (2-AEC); and/or it is insensitive to feedback inhibition with lysine. A skilled worker can readily determine whether a given DHPS polypeptide exhibits a detectable amount of a desired function or property, using conventional procedures.

The amino acid sequence of a DHPS polypeptide from *E. coli* is AAA23665 [gi:145708] (SEQ ID NO: 3).

```
  1 mftgsivaiv tpmdekgnvc raslkklidy hvasgtsaiv
    svgttgesat lnhdehadvv 61 mmtldladgr ipviagtgan ataeaisltq rfndsgivgc
    ltvtpyynrp sqeglyqhfk 121 aiaehtdlpq ilynvpsrtg cdllpetvgr lakvkniigi
    keatgnltrv nqikelvsdd 181 fvllsgddas aldfmqlggh gvisvttnva ardmaqmckl
    aaeehfaear vinqrlmplh 241 nklfvepnpi pvkwackelg lvatdtlrlp mtpitdsgre
    tvraalkhag ll
```

The amino acid sequence of a wild-type DHPS polypeptide from soybeans is AAA73555.1(gi:548321) (SEQ ID NO: 4).

```
  1 mitnsaavkp nfhlpmrsfe lknrtspedi kalrlitaik
    tpylpdgrfd leayddlvnm 61 qigqgaegvi vggttgegql msweehiili ahtvncfggk
    ikvigntgsn streaihate 121 qgfavgmhaa lhinpyygkt sldgmvahfr svlsmgptii
    ynvpartgqd ipphviqtla 181 esvnlagvke cvgndrikqy tddgivvwsg nddqchdarw
    gygatgvvsv asnlvpglmr 241 elmfggvnpt lnskllplid wlfhmpnpig lntalaqlgv
    irpvfrlpfv plpvdkrief 301 anlvkeigre hfvgnkvvev lddddfflvs ry
```

The amino acid sequence below (SEQ ID NO: 5) is a modified portion of the sequence of SEQ ID NO: 4 in which amino acid 84 is changed to arginine, starting from amino acid 54 of the soybean DHPS. Amino acid 84 is changed to arginine i.e., the 30th amino acid in the sequence shown (SEQ ID NO: 5), indicated by the bold letter "R."

```
YDDLVNMQIG QGAEGVIVGG TTGEGQLMSR EEHIILIAHT
VNCFGGKIKV

IGNTGSNSTR EAIHATEQGF AVGMHAALHI NPYYGKTSLD
GMVAHFRSVL

SMGPTIIYNV PARTGQDIPP HVIQTLAESV NLAGVKECVG
NDRIKQYTDD

GIVVWSGNDD QCHDARWGYG ATGVVSVASN LVPGLMRELM
FGGVNPTLNS

KLLPLIDWLF HMPNP
```

A "functional" DHPS polypeptide may comprise SEQ ID NO: 3 or SEQ ID NO: 4 modified as shown in SEQ ID NO:5; or it may comprise any of a number of variants of those sequences, either naturally occurring or deliberately generated, provided that the changes do not substantially alter a function or property as discussed above.

For example, the functional DHPS polypeptide may be shorter or longer than one of the above polypeptides. In embodiments of the invention, the variant DHPS differs from SEQ ID NO: 3 or SEQ ID NO: 4 by one or more modifications, which are either conservative or non-conservative modifications (e.g., insertions, deletions, additions and/or substitutions). By "conservative substitutions" is meant by combinations such as Gly, Ala; Val, Ile, Leu; Asp, Glu; Asn, Gln; Ser, Thr; Lys, Arg; and Phe, Tyr. Variants can include, e.g., homologs, muteins and mimetics. Many types of protein modifications, including post-translational modifications, are included. Post-translational modifications include naturally occurring or synthetically produced, covalent or aggregative conjugates with other chemical moieties, e.g., glycosyl groups, lipids, phosphates, acetyl groups, etc., as well as cleavage, such as of terminal amino acid(s). See, e.g., modifications disclosed in U.S. Pat. No. 5,935,835. Other functional variants may comprise added peptide sequences, either naturally occurring or heterologous, such as, e.g., leader, signal, secretory, targeting, enzymatic etc. sequences. In one embodiment, a functional variant DHPS polypeptide exhibits at least about 70% sequence identity (e.g., at least about 80%, 90%, 95%, 98% or 99% sequence identity) to SEQ ID NO: 3 or SEQ ID NO: 4 or SEQ ID NO: 5.

As *E. Coli* DHPS is naturally resistant to 2-AEC no modifications are required. However, with respect to soybean DHPS, as guidance as to which amino acids can be altered without substantially altering the function of the DHPS, the following amino acids of SEQ ID NO: 3, SEQ ID NO: 4, or SEQ ID NO: 5 have been modified to impart lysine resistance to soybean DHPS enzyme (Silk G. W. and B. F. Matthews, 1997, Plant molecular biology, 33:931-933) and can be expected to confer (or to contribute to) resistance to AEC (referring to SEQUENCE ID NO: 4):

amino acid 104 (ASP)
amino acid 112 (ALA).

Changes of other amino acids are less likely to affect this function of the protein, and thus are more amenable to alteration.

A polynucleotide which encodes a functional variant DHPS of the invention may differ from the sequence of SEQ ID NO: 1 or SEQ ID NO: 2 in a variety of ways. For example, the sequence may exhibit a percent identity to one of those sequences of at least about 70% (e.g., at least about 80%, 90%, 95%, 98% or 99% sequence identity).

The comparison of sequences and determination of percent identity and similarity between two sequences (either polypeptide or polynucleotide) can be accomplished using any of a variety of conventional mathematical algorithms. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Among the many types of suitable mathematical algorithms are those described in Karlin et al. (1993) Proc. Natl. Acad. Sci. USA 90:5873-5877; the algorithm incorporated into the NBLAST and XBLAST programs (version 2.0) as described in Altschul et al. (1997) Nucleic Acids Res. 25:3389-3402; the GAP program I the GCG software package (Devereux et al. (1984) Nucleic Acids Res. 12 (1):387); and the algorithm of Myers and Miller, CABIOS (1989). Alternatively, a functional variant polynucleotide of the invention may hybridize specifically to a polynucleotide having SEQ ID NO: 1 or SEQ ID NO: 2 under conditions of high stringency. Conditions of "high stringency," as used herein, means, for example, hybridization in a hybridization solution containing, e.g., about 5×SSC, 0.5% SDS, 100 μg/ml denatured salmon sperm DNA and 50% formamide, at 42° C.

As used herein, the term "expression control sequence" means a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. An expression control sequence may be linked to another expression control sequence. For example, a tissue-specific expression control sequence may be linked to a basal promoter element or to an enhancer that conveys high levels of expression.

Any of a variety of expression control sequences can be used in constructs of the invention; suitable expression control sequences will be evident to the skilled worker.

In preferred embodiments of the invention, the "first" expression control sequence (regulating the expression of the DHPS sequence) comprises a constitutive promoter, which is expressed constitutively in a wide variety of cell types. Preferably, the promoter is sufficiently strong to produce enough DHPS to generate sufficient levels of lysine to achieve cell growth in the presence of added AEC. Among the suitable strong constitutive promoters/enhancers are expression control sequences from ribosomal RNA promoters or, most preferably, from the CaMV 35S promoter.

In embodiments of the invention, the "second" expression control sequence (regulating the expression of the polypeptide of interest) comprises a tissue specific promoter, most preferably a promoter which is active specifically in seeds (a "seed-specific" promoter). Typical examples are glycinin, phaseolin, conglycinin, seed lectin, napin, zein or other seed-specific promoters Both constitutive and tissue-specific promoters isolated from one plant function generally in a wide variety of other plants; thus, expression control sequences from a variety of plant species are suitable for expression in soybeans.

In a most preferred embodiment, the "first" expression control sequence (driving expression of the DHPS sequence) comprises a constitutive promoter; and the "second" expression control sequence (driving expression of the heterologous polypeptide of interest) comprises a seed specific promoter.

In some embodiments of the invention, the DHPS-encoding sequence and/or the sequence encoding the polypeptide of interest are not operably linked to an expression control sequence. In such a case, the polypeptide integrates near an endogenous expression control sequence in the plant, and its expression is regulated by that endogenous expression control sequence. For example, an exogenously introduced polynucleotide may integrate at a random site in the soybean genome, by illegitimate recombination; or a DHPS sequence from *E. coli* may integrate at the site of similar sequences of the endogenous soybean DHPS gene by homologous recombination.

Additional coding sequences may be included, such as a transit peptide that targets the polypeptide of interest to go to the desired organelle, such as a chloroplast. For example, Pea RbcS transit peptide is used to target the *E. coli* DHPS to chloroplasts where the lysine biosynthesis pathway is operative. Other desirable coding sequences will be apparent to a person of ordinary skill in the art.

An embryogenic culture comprising the above-discussed sequences encoding DHPS and the polypeptide of interest is "contacted" by the AEC by any of a variety of conventional means. These include, e.g., incorporation of AEC into the liquid or solid culture media. Methods for allowing the embryos to grow to form plants and to pollinate and produce seeds (beans) are conventional in the art.

In preferred embodiments of the invention, the DHPS and heterologous nucleic acids are stably integrated into the genome of the plant. However, in other embodiments, these nucleic acids are introduced into the embryo on minichromosomes and are maintained stably, and are transmitted through the germ line.

"Genome" is intended to refer to the chromosomes in the nucleus of the soybean plant but also any autonomously replicating DNA that is passed to daughter cells, e.g. in chloroplasts and mitochondria.

Selection effective conditions are those that inhibit growth of non-resistant embryos, and are effective to grow transformants selectably, e.g. a concentration and formulation of AEC sufficient to slow the growth of non-transformed embryo cells while permitting transformed embryo cells to grow better than non-transformed embryo cells, under the same conditions, preferably under conditions where the non-transformed cells do not grow at all and transformed cells grow well, e.g. an AEC concentration of 1 mM.

In a preferred embodiment of the invention, the polynucleotide encoding the DHPS polypeptide (which is operably linked to the first expression control sequence) and the polynucleotide encoding the polypeptide of interest (which is operably linked to the second expression control sequence) are on the same plasmid. The sequence encoding the functional DHPS polypeptide may be either upstream or downstream of the sequence encoding the heterologous polypeptide of interest. In another embodiment, the two polynucleotides are on separate plasmids.

A wide variety of heterologous "polypeptides of interest" will be evident to the skilled worker. These can be, e.g., "input" genes (such as genes conveying herbicide resistance, etc.) or "output" genes (such as genes that provide a nutritional trait, increased oil content, proteins, etc.) Input traits are traits that benefit growers such as better or easier weed control, insect or disease resistance etc. Output traits benefit processors or consumers such as healthier or more stable oil, protein higher in limiting amino acids such as methionine, lower in oligosaccharides or phytate, etc. Among suitable polypeptides of interest are, e.g., omega-3 desaturase; a polypeptide providing improved meal amino acid compositions; a polypeptide imparting resistance to a bacterium, a fungus, a virus, an insect, or a nematode; a polypeptide providing herbicide resistance; a polypeptide affecting soybean composition or quality; a polypeptide that enhances nutrient utilization; or a polypeptide providing resistance to environmental factors (such as drought) or stress. More particularly, the polypeptide can be phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase or glyphosate oxidoreductase. Other preferred heterologous polypeptides of interest include a lysophosphatidate acyl transferase (LPAT); a diacylglycerol acyltransferase (DGAT); a polypeptide which provides increased oil content in the soybean; delta-9 desaturase (which can result in a decreased saturated fatty acid contents in the soybean plant, resulting in palmitoleic acid accumulation in the soybean plant); and delta-12 desaturase (which can result in high oleic acid content soybean oil); and DHPS.

The DHPS-encoding sequence which is operably linked to the first expression control sequence may take any of a variety of forms. Generally, the sequence encodes a DHPS that is resistant to AEC inhibition, such as a sequence isolated from a bacterium (e.g., *Escherichia coli*), or a sequence isolated from *Corynebacterium glutamicum* or *Nicotiana sylvestris*. In a preferred embodiment, the DHPS-encoding sequence is isolated from *E. coli*, and is represented by SEQ ID NO: 2. In other embodiments of the invention, the DHPS-encoding sequence is a sequence that has been genetically altered from a wild type sequence to become resistant to AEC inhibition. A variety of possible such alterations are discussed above. A preferred such variant is the mutant version of the endogenous soybean sequence which is discussed in the Examples and whose coding sequence is represented by SEQ ID NO: 1.

In embodiments of the invention, a 3' terminator sequence (e.g., a polyA addition and/or a RNA cleavage sequence) is located 3' to one or both of the DHPS-encoding sequence and the sequence encoding the heterolgous polypeptide of interest. The skilled worker will be aware of a number of suitable terminator sequences. These include, e.g., a pea RUBISCO 3' controlling sequence, a ribosomal RNA terminator, or a 3' transcription region for the nopaline synthase (NOS) gene.

In embodiments of the invention, one or both of the sequence encoding the functional DHPS polypeptide and the sequence encoding the heterologous polypeptide of interest is operably linked to two or more expression control sequences. For example, a minimal promoter and some sort of enhancer would normally be needed. In embodiments of the invention, a transgenic soybean plant produced as above is further backcrossed to generate a transgenic soybean plant which is homozygous for the sequence encoding the heterologous polypeptide of interest. If the gene encoding the polypeptide of interest is dominant, it is, of course, not necessary for the gene to be homozygous in order for it to express functional proteins. However, because soybean plants are generally sold as inbred lines, which breed true, it is preferable that the plants (and seeds derived therefrom) be homozygous for these heterologous genes. Methods for performing suitable backcrosses are conventional, and suitable crosses will be evident to the skilled worker.

In embodiments of the invention, suitable backcrosses are performed in order to generate a transgenic soybean plant which is homozygous for the sequence encoding the DHPS polypeptide. Homozygosity of these genes is not required for future growth of plants (or seeds therefrom) which express heterologous polypeptides of interest. In fact, the selectable marker at this stage can even be absent. However, as discussed more fully below, in some embodiments of the invention, DHPS is expressed constitutively, at high levels, in order to protect the plant against inhibition by AEC, thereby allowing the use of AEC as a pesticide. In these embodiments, it is preferable that the DHPS is homozygous in the plant.

In embodiments of the invention, the transgenic plant is fertile. However, in other embodiments (e.g., when the leaves are to be used), the plant does not need to be fertile.

The method may include using a transformation vector, which comprises the DHPS coding sequence, an appropriate expression control sequence (such as a strong constitutive promoter such as the 35S promoter) and optionally, a terminator/3' controlling region. The vector also comprises a gene of interest for soybean improvement and/or may include other genes for amplification, e.g. a gene for selection in *E. coli*, which can be the DHPS gene itself in an appropriate auxotroph.

The resultant soybean plant is one expressing a functional DHPS gene that is resistant to AEC levels that inhibit growth of normal soybean cells or tissues. A gene of interest may include lysophosphatidate acyl transferases (LPATs), diacylglycerol acyltransferases (DGATs), both to increase oil contents; delta-9 desaturases to decrease saturated fatty acid contents and/or to achieve palmitoleic acid accumulation; delta-12 desaturases for high oleic acid soybean oil; omega-3 desaturases; genes for improved meal amino acid compositions; genes for disease, insect and nematode resistance; genes for herbicide tolerance; genes for drought resistance and other genes for soybean improvement.

The DHPS gene may be a functional bacterial DHPS gene that is resistant or tolerant to AEC.

An advantage of the inventive method and plants is that selected plants including AEC-resistant DHPS genes can be resistant to growth inhibitory concentrations of AEC in field use. This permits use of a novel herbicide that can be produced from natural sources, and may be appropriate for organic farming. See Example 4. In particular, this may be used for weed control both in crop fields wherein the crops are selected for resistance to AEC or Lysine and Threonine or around trees, flowers and other plants, where contact to foliage is minimized as well as around buildings and other structures.

Examples of suitable DHPS genes include: *Corynebacterium glutamicum* (e.g., Cremer J, Treptow C, Eggeling L, Sahm H., Regulation of enzymes of lysine biosynthesis in *Corynebacterium glutamicum*, J Gen Microbiol. December 1988; 134 (Pt 12):3221-9, Nucleotide sequence of the dapA gene from *Corynebacterium glutamicum*; Bonnassie S, Oreglia J, Sicard A M. Nucleic Acids Res. Nov. 11, 1990; 18(21): 6421), *Escherichia coli* (e.g., Laber B, Gomis-Ruth F X, Romao M J, Huber R, *Escherichia coli* dihydrodipicolinate synthase. Identification of the active site and crystallization, Biochem J. Dec. 1, 1992; 288 (Pt 2):691-5.) or *Nicotiana sylvestris* (e.g., Ghislain, M., Frankard, V., Jacobs, M. 1995 A dinucleotide mutation in dihydrodipicolinate synthase of *Nicotiana sylvestris* leads to lysine overproduction, *Plant J.*, 8, 733 743).

A variety of types of expression control sequences (e.g., promoters) and terminator sequences known to one skilled in the arts that can be used, such as any strong constitutive or nearly constitutive expression control sequence and terminator. For example expression control sequences may include a 35S promoter or ribosomal RNA gene promoters. Terminator sequences may include pea RUBISCO 3' controlling sequences or Nos terminator sequences.

A variety of AEC concentrations can be used for the selection of bacterial DHPS transformed soybean somatic embryos, so long as those concentrations are in an amount that would inhibit the growth of soybean seeds or somatic embryos without the AEC resistant DHPS gene. For example, at least about 0.1 mM or higher may be sufficient to inhibit growth, and 1 mM or higher can stop all cell growth. Higher concentrations than about 10 mM may inhibit growth even in transformed embryos. AEC concentrations for selection can be from about 0.5 mM to about 5 mM, 1.0 mM to about 5 mM, 2.5 mM to about 5 mM, or more than or less than about 0.5 mM, 1 mM, 1.5, mM, 2 mM, 2.5 mM, 3.0 mM, 3.5 mM, 4.0 mM, 4.0 mM or 5.0 mM. Concentrations in the range up to about 10 mM or 20 mM may be suitable for selection in some circumstances. In later growth stages and including field use, the higher concentrations of AEC may be preferred, in conjunction with surfactants or other uptake enhancers.

Figure 6A:
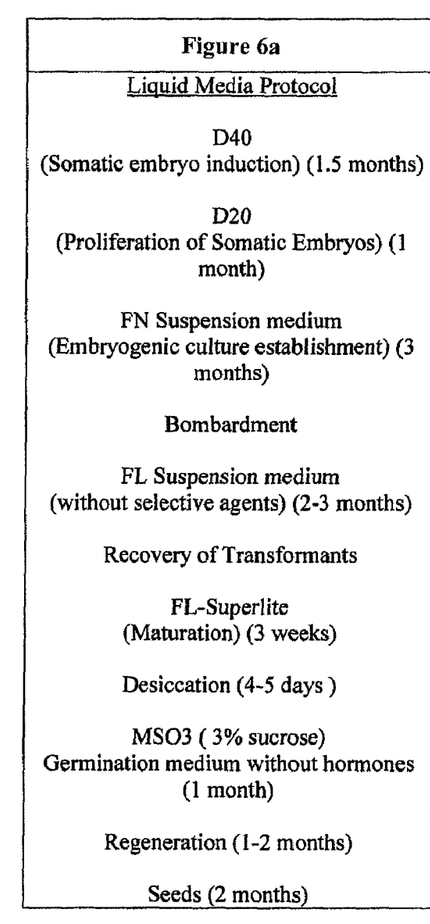
FIGS. 6a and 6b show protocols for the transformation of soybean by particle bombardment using liquid (6a) and solid (6b) media protocols.
Figure 6B:
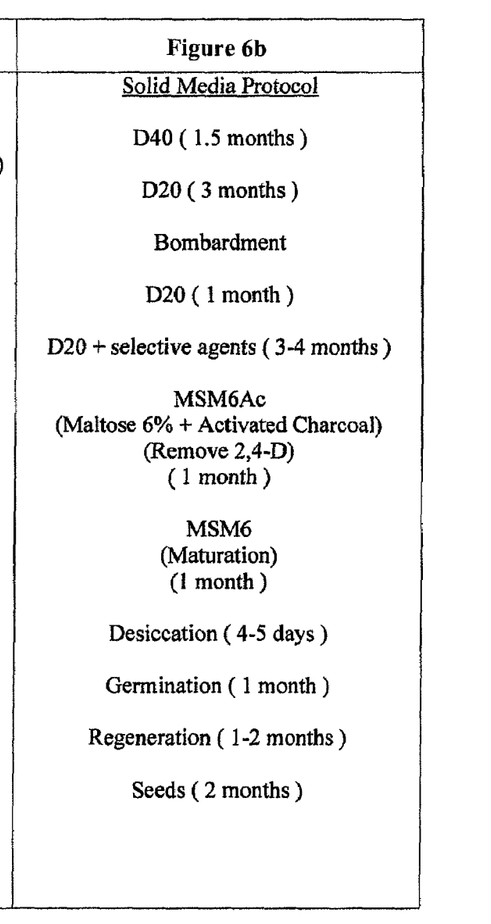

A variety of transformation protocols may be used with the inventive process. For example, FIGS. 6a and 6b show the transformation of soybean by particle bombardment using liquid and solid media protocols using somatic embryos (Trick et al., 1997). Once embryogenic cultures are established, one can get plenty of material with a liquid medium based protocol for transformation. However, with older cultures the regenerated plants are mostly sterile (Hazel et al., 1998). With solid medium-based protocols somatic embryos need to induced regularly. The maturation of somatic embryos on MSM6 medium takes much longer than with liquid medium based protocols with FL-Superlite (Samoylov et al., 1998).

Targeting cells that can give rise to whole plants for transformation and selection of whole plants is quite difficult with soybeans. Kanamycin selection which works well with most plants does not work at all with soybeans. The precise reasons of why some plants such as soybeans are so recalcitrant to standard transformation and regeneration systems are unknown, except that it is thought that many more cells in plants such as soybeans are terminally differentiated compared with easier plants such as potatoes or tobacco.

Suitable transformation vectors known to one skilled in the art can be used with the inventive process. For example, the Binary vector pCAMBIA-1201, Genbank # AF234293, which may be obtained from Cambia group in Australia. Before cloning pCambia1201, the DHPS gene can be cloned along with pea rbcs chloroplast transit peptide into another binary vector pKalyx. This is done to clone the *E. coli* DHPS gene along with transit peptide under 35S promoter. This vector has a Nos terminator.

The accession number is gi|145707|gb|M12844.1 for the following *E. coli* DHPS sequence (SEQ ID NO: 2):

```
  1 ccaggcgact gtcttcaata ttacagccgc aactactgac
    atgacgggtg atggtgttca 61 caattccacg gcgatcggca cccaacgcag tgatcaccag
    ataatgtgtt gcgatgacag 121 tgtcaaactg gttattcctt taaggggtga gttgttctta
    aggaaagcat aaaaaaaaca 181 tgcatacaac aatcagaacg gttctgtctg cttgctttta
    atgccatacc aaacgtacca 241 ttgagacact tgtttgcaca gaggatggcc catgttcacg
    ggaagtattg tcgcgattgt 301 tactccgatg gatgaaaaag gtaatgtctg tcgggctagc
    ttgaaaaaac tgattgatta 361 tcatgtcgcc agcggtactt cggcgatcgt ttctgttggc
    accactggcg agtccgctac 421 cttaaatcat gacgaacatg ctgatgtggt gatgatgacg
    ctggatctgg ctgatgggcg 481 cattccggta attgccggga ccggcgctaa cgctactgcg
    gaagccatta gcctgacgca 541 gcgcttcaat gacagtggta tcgtcggctg cctgacggta
    accccttact acaatcgtcc 601 gtcgcaagaa ggtttgtatc agcatttcaa agccatcgct
    gagcatactg acctgccgca 661 aattctgtat aatgtgccgt cccgtactgg ctgcgatctg
    ctcccggaaa cggtgggccg 721 tctggcgaaa gtaaaaaata ttatcggaat caaagaggca
    acagggaact taacgcgtgt 781 aaaccagatc aaagagctgg tttcagatga ttttgttctg
    ctgagcggcg atgatgcgag 841 cgcgctggac ttcatgcaat tgggcggtca tggggttatt
    tccgttacga ctaacgtcgc 901 agcgcgtgat atggcccaga tgtgcaaact ggcagcagaa
    gaacattttg ccgaggcacg
```

```
 961  cgttattaat cagcgtctga tgccattaca caacaaacta
      tttgtcgaac ccaatccaat 1021  cccggtgaaa tgggcatgta aggaactggg tcttgtggcg
      accgatacgc tgcgcctgcc 1081  aatgacacca atcaccgaca gtggtcgtga gacggtcaga
      gcggcgctta agcatgccgg 1141  tttgctgtaa agtttaggga gatttgatgg cttactctgt
      tcaaaagtcg cgcctgg
```

The coding sequence which starts at 272 and ends at 1150 was used.

The effect of AEC on proliferating somatic embryos were conducted in both liquid and solid media and methylated seed oil may be added as a surfactant to facilitate AEC absorption. MSO concentration may be about 0.0007%. However, even without MSO, AEC may be effective in growth inhibition of soybean somatic embryos.

There are a variety of different sources/suppliers from which to obtain AEC, e.g., Sigma, and there are several published procedures for its synthesis. AEC is a lysine analog that naturally occurs in the mushroom *Rozites caperta* (Matsumoto, 1984; Cadogan et al., 1996) (also, see Example 4).

Suitable transformation methods known to one skilled in the art can be used. One of the well established soybean transformation procedures is gene gun bombardment of somatic embryos (Finer and McMullen, 1991). The bombarded embryos are be selected with a selectable marker on the introduced DNA. So far for soybean selection the antibiotic hygromycin is the one mostly in use. Known methods are adapted to eliminate antibiotic resistance genes commonly included on existing vectors, while permitting amplification (growth) of the vector plasmids. For example, gene gun transformation has traditionally used the entire cloning plasmid including an antibiotic resistance gene for selection in *E. coli* but a restriction site can be included so that after amplification, the antibiotic resistance gene section can be cut out, leaving the DHPS gene and the gene of interest to be used for bombardment into the cells.

For another example, with Agrobacterium mediated transformation normally only DNA between the T-left and T-right borders is incorporated into plant chromosomes. Accordingly, the antibiotic resistance gene(s) for bacterial selection can be placed outside these borders so that they are not inserted into the target cells by the transformation process.

For a third example, one can flank genes that are not wanted in post-transformation target plant chromosomes with CRE sites, so that crossing the resulting transgenic plants containing inserted LOX genes will cause the genes flanked with CRE sites to be cleaved out in subsequent generations.

No antibiotic resistance genes are needed for cloning in *E. coli* auxotrophic for DHPS. A preferred method is to amplify such antibiotic-resistance gene-free vectors in *E. coli*, and then use gene gun bombardment for transformation.

An improved soybean seed according to the invention can be planted in an open field. AEC is applied during germination, growth, and/or maturation to eliminate weeds. Soybeans are harvested from the mature plant, having improved output traits. The DHPS gene used to confer AEC resistance can be derived from a soybean, and the AEC that is used can be obtained from natural sources, permitting the harvested soybeans to be marketed more readily than transgenic soybeans having heterologous genes, antibiotic resistance genes, or glyphosate or other herbicide resistance genes that require use of synthetic herbicides.

Regeneration of soybean plants via somatic embryogenesis can be done by the following steps: (a) Immature zygotic embryo cotyledon explants are grown on medium containing 40 mg/L 2,4-D (D40 medium), (b) Somatic embryo induction is carried out on D40 medium, (c) Somatic embryo proliferation is carried out on D20 medium, (d) Matured cotyledonary stage embryos are grown on medium containing 6% maltose (MSM6), (e) Desiccation of matured embryos is carried out, (f) Germination is carried out on medium containing 3% sucrose (MSO3), (g) Germinated somatic embryo are produced with well defined root and shoot system, and (h) Regenerated soybean plants are transferred to soil.

EXAMPLES

Example 1

As a first step in the selection, different concentrations of AEC were used to see if it can kill the proliferating soybean somatic embryos as well as tobacco leaves and germinating tobacco and soybean seeds and germinating soybean somatic embryos. The effect of AEC is clearly seen in all these cases with varying concentrations. 100 μm AEC is sufficient to completely inhibit the germination of soybean somatic embryos whereas for germinating soybean seeds and tobacco seeds 2.5 mM AEC is required. For proliferating soybean somatic embryo concentrations up to 1 mM AEC is needed along with 0.0075% methylated seed oil to kill them. To further confirm that AEC is acting on the above mentioned tissues, the *E. coli* DHDPS gene was cloned and put into the binary vector p1201 with the pea RBCs transit peptide under the CaMV 35S promoter.

Proliferating soybean somatic embryos were shot with a gene gun using the *E. coli* DHDPS gene construct and the embryos were selected on both solid D20 and liquid F1 cv Jack proliferating media with 1 mM to 2.5 mM AEC with 0.0075% methylated seed oil. The positive looking green clumps were put on the MSM6AC maturation medium. Some of the embryos have been shown to contain an introduced GUS gene indicating the soybean transformation with AEC as a selective agent can be achieved.

Example 2

Lysine-Threonine and Lysine-Analog S-(2-aminoethyl)-L-cysteine as Alternative Non-Antibiotic Selection System for Soybean Somatic Embryos.

Introduction

Plant cells and tissues are normally killed by exposure to S-2-aninoethyl-cysteine (AEC), which prevents lysine synthesis through inhibition of the plant enzyme dihydrodipicolinate synthase (DHPS). *E. Coli* DHPS is not inhibited by AEC. A vector for producing transgenic soybean plants encodes *E. Coli* DHPS. Soybean cells and tissues that are successfully transfected with the vector can be identified by exposure to AEC, which kills cells and tissues not containing the gene encoding *E. Coli* DHPS.

Procedure

An AEC selection system for soybean seeds with precise genetic changes and model system seeds (for rapid system validation) were germinated on 2 mM and 5 mM AEC containing agar plates. On the control plates without AEC all the seeds germinated, however only ~10% of the soybean seeds germinated on 2 mM AEC plates and none on 5 mM plates. Not a single model system seed germinated at either of these concentrations.

The effect of AEC on soybean somatic embryos were checked at two stages (1) during the germination (2) during proliferation. The AEC effect during germination was very effective with concentrations above 100 μM were enough to prevent the germination completely.

However, selection during proliferation is always a better way as selected clones can be proliferated and the untransformed embryos can be killed in the earlier stages itself. Unfortunately concentrations up to 20 mM were not sufficient to kill most of the proliferating embryos, though some of the embryos turned yellowish and developed brown spots, but many of them continued to proliferate like controls even after two changes of the medium, once every 15 days. To find out if surfactants can help in AEC absorption during proliferation a methylated seed oil based surfactant was used. A series of experiments were run with liquid proliferation medium to determine a suitable surfactant concentrations as the 0.2% which was used initially killed the cells even without AEC addition to the medium. It was determined that a 0.005% concentration is suitable to use with AEC. However on solid medium with 0.2% surfactant both controls and 10 mM AEC cultures remained green with growth for two weeks before they died. The cultures on plates with 20 mM AEC died in 4 days indicating solid medium selection can be useful.

To test if the modified soy DHDPS can become insensitive to AEC and whether 18:1 desaturases can function as a 16:1 desaturase, experiments were conduced with E. Coli auxotrophs. A DHDPS auxotroph was obtained from the E. coli genetic center that can be rescued on medium without diaminopimelic acid when transformed with lysine insensitive DHPS and not with the wild type gene. Similarly, the E. coli auxotroph (fabA/fadR mutant) was obtained which can be complimented by $C_{14}$ and $C_{16}$ ACP desaturases but not by stearoyl-ACP desaturases. The primers required for cloning were designated and obtained from soybean genes. A suitable E. coli expression vector was obtained to express these genes in the respective auxotrophs.

Summary

Experiments were conducted with different tissues of soybean to determine whether LT and AEC can be used as selection agents. Both AEC and LT can inhibit seed as well as soybean somatic embryos (SSE) germination. AEC concentrations of 1.5 to 2.5 mM are effective for selection in presence of 0.075% MSO (methylated seed oil) as surfactant. However LT (up to 10 mM) were not able to inhibit growth of proliferating SSE. Soybean SE and tobacco transformed with wild-type E. coli DHPS are found to be resistant to normally lethal concentrations of AEC. Green proliferating transgenic somatic embryos were found to be selected at the concentration level of 2.5 mM AEC. Similarly, selection at low micro molar AEC and 1.5 mM LT resulted in transgenic tobacco shoots. These transgenic SS embryos and tobacco shoots were also observed to be GUS positive indicating resistance to AEC can be used as a selection system for soybean and tobacco.

Results

To determine whether AEC can be developed as a selectable marker for soybeans the effect of different concentrations of AEC was examined on the germination of soybean seeds and matured soybean somatic embryos and on proliferating soybean somatic embryos. The effect of AEC is clearly seen in all these cases with varying concentrations. The effect of AEC was also examined as a herbicide against pigweed, foxtail and tobacco.

Figure 1:
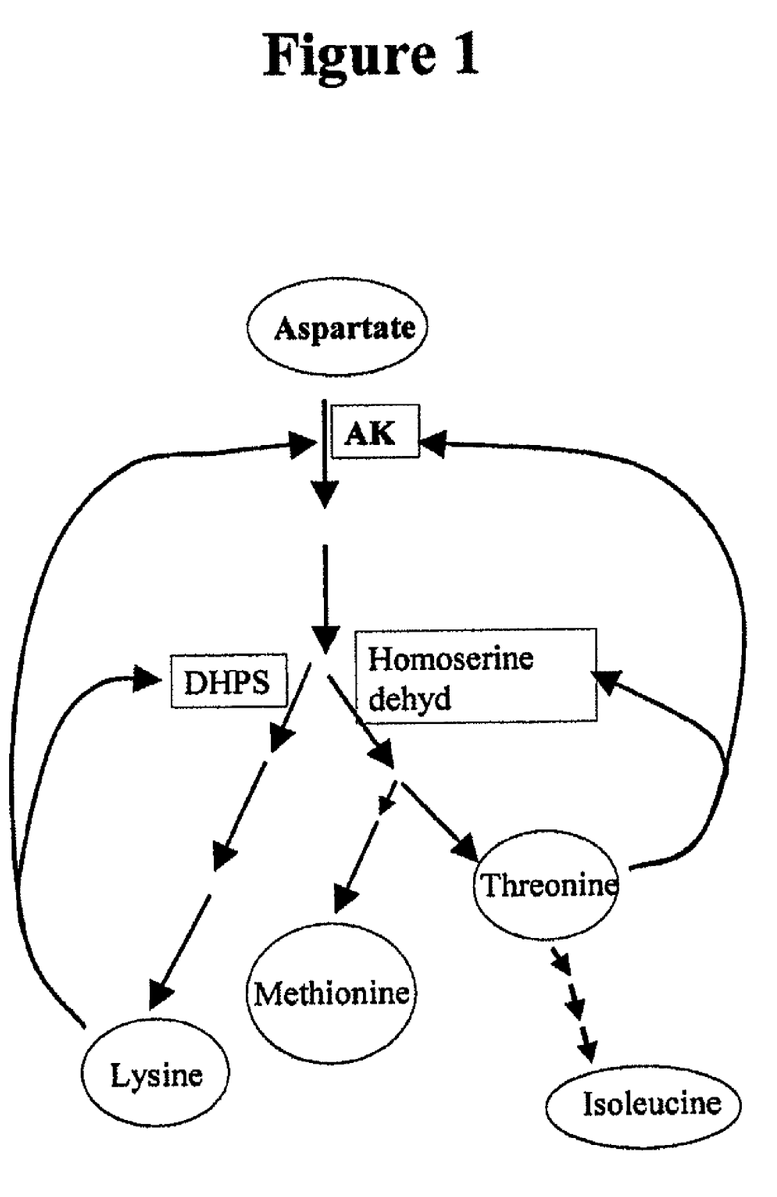
FIG. 1 diagrams the biosynthesis pathway of aspartate-derived amino acids.
Figure 2:
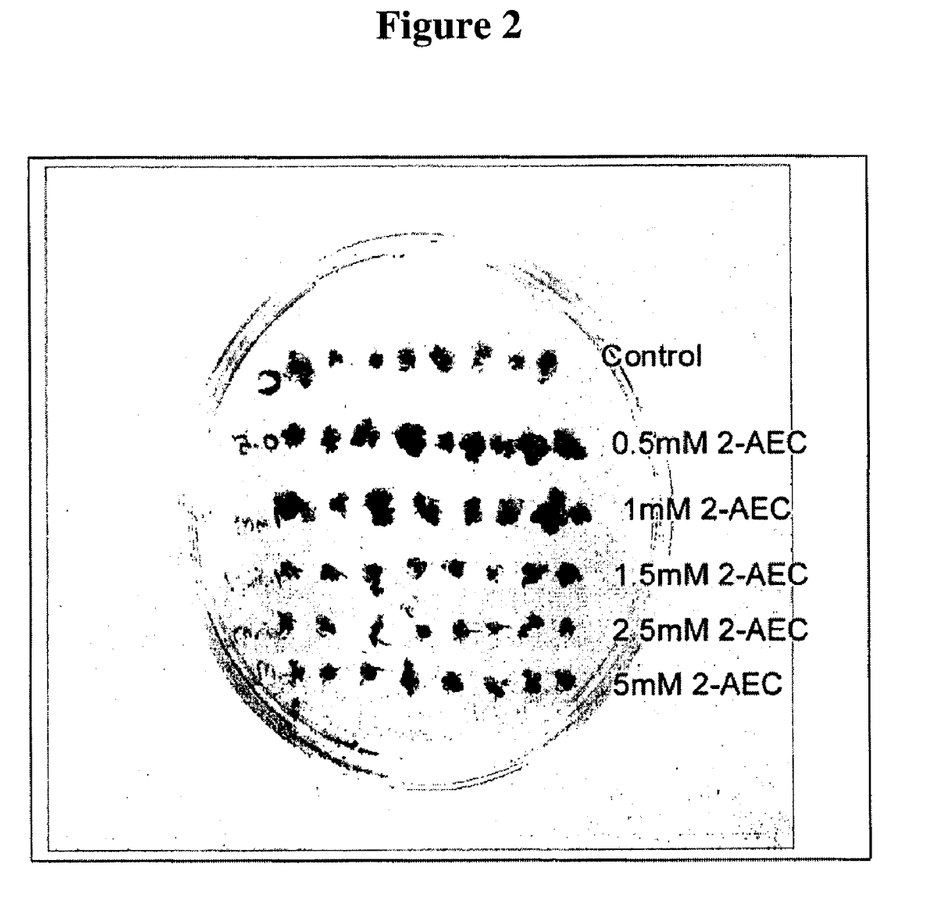
FIG. 2 shows the use of 0.5 mM, 1.0, mM, 1.5, mM, 2.5 mM and 5.0 mM concentrations of AEC and illustrates that 1.5 mM AEC is sufficient to kill proliferating soybean somatic embryos on ⅕th D20 medium (⅕MS salts, ⅕B5 vitamins and 20 mg/L 2,4-D).

Five mM AEC can prevent the germination of soybean seeds; 2.5 mM is quite effective. 500 μM AEC completely prevented the germination of soybean somatic embryos; 100 μM AEC was quite effective. FIG. 2 shows the use of 0.5 mM, 1.0, mM, 1.5, mM, 2.5 mM and 5.0mM concentrations of AEC and illustrates that 1.5 mM AEC is sufficient to kill proliferating soybean somatic embryos on ⅕th D20 medium (⅕ MS salts, ⅕ B5 vitamins and 20 mg/L 2,4-D). Spray studies have been done using major dicot and monocot weeds, pigweed (Amaranthus retroflexus) and giant foxtail (Setaria faberi) in addition to tobacco. These experiments using 7 to 10 day old seedlings show 20 mM AEC is lethal to pigweed, foxtail and tobacco.

Figure 3:
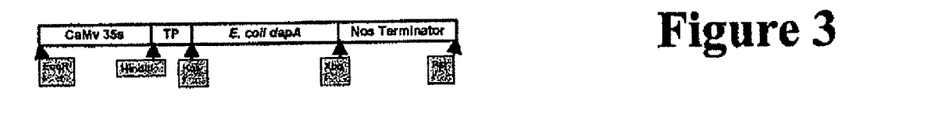
FIG. 3 shows a transformation vector using a Pea RbcS transit peptide to target the *E. coli* DHPS to chloroplasts where the lysine biosynthesis pathway is operative.

FIG. 3 shows a transformation vector using Pea RbcS transit peptide to target the E. coli DHPS to chloroplasts where the lysine biosynthesis pathway is operative.

Figure 4:
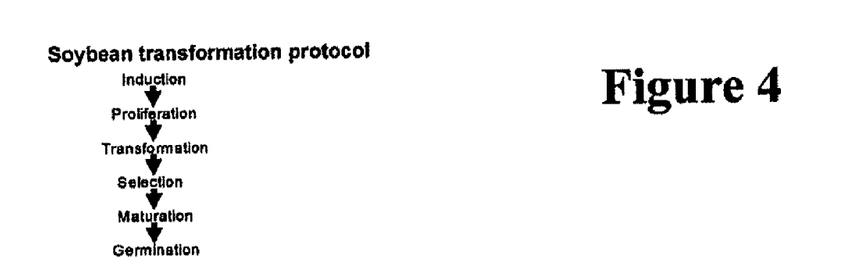
FIG. 4 is a schematic flowchart indicating that soybean somatic embryos were induced from immature zygotic embryos on MS plates containing 40 mg/L 2,4-D. Induced embryos are proliferated either on solid D20 (20 mg/L 2,4-D) or FL Jack liquid medium (10 mg/L 2,4-D). Then green clumps are bombarded with DNA coated gold particles using PD-1000 particle bombardment system (a.k.a. "Genegun"). Embryos are selected with 2.5 mM AEC on ⅕ D20 plates. Positive looking green clumps were proliferated, matured. These embryos were stained for GUS and checked for the expression of *E. coli* DHPS gene to confirm the positive transformants. The resulting plants germinate and grow.

In FIG. 4, SS embryos were induced from immature zygotic embryos on MS plates containing 40 mg/L 2,4-D. Induced embryos are proliferated either on solid D20 (20 mg/L 2,4-D) or FL Jack liquid medium (10 mg/L 2,4-D). Then green clumps are bombarded with DNA coated gold particles using PD-1000 particle bombardment system (a.k.a. "Genegun"). Embryos are selected with 2.5 mM AEC on ⅕ D20 plates. Positive looking green clumps were proliferated, matured. These embryos were stained for GUS and checked for the expression of E. coli DHPS gene to confirm the positive transformants.

GUS staining of DHPS transgenic embryos has been done.

Figure 5:
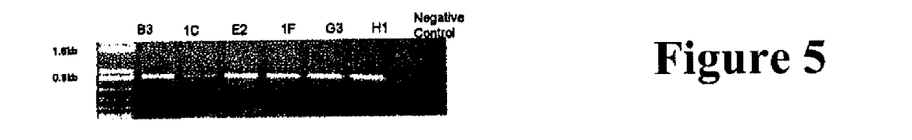
FIG. 5 demonstrates the expression of *E. coil* DHPS in different transgenic soybean somatic embryo lines and negative control embryos.

FIG. 5 demonstrates the expression of E. coli DHPS in different transgenic soybean somatic embryo lines and negative control embryos.

Discussion

The AEC selection results showed that AEC can be successfully used as a selection marker for soybeans. The added advantage of this selection system besides being a non-antibiotic selection marker is that it could increase the levels of essential amino acid lysine. No problems were faced in the maturation and germination of these transgenic embryos. When the effect of AEC was tested at the whole plant level, 20 mM AEC was sufficient to kill fox tail and tobacco and effectively prevented the growth of pig weed.

Conclusion

The lysine analog AEC is a successful non-antibiotic selectable marker for the transformation of soybean somatic embryos.

Example 3

SEQ ID No. 1:
ctttggactctgaagctatgatgacttggtgaatatgcagattggacaag gggctgaaggtgttattgttggtgggacaactggtgaaggccaattaatg agccgggaagagcacataatacttattgctcatacagtcaactgttttgg tgggaaaattaaggttattggaaatactggaagcaactccaccagggaag caattcatgccactgagcagggttttgctgttggaatgcatgctgcccctt cacataaacccttactatggcaaaacctccttggatggtatggttgctca ctttcgaagtgtgctttccatgggacccacaataatctacaatgtgcctg

```
-continued
cacggaccggacaagacattcctccgcatgtaattcaaaccttagctgaa agtgttaacctggctggtgtcaaggagtgtgtgggaaatgaccgaatcaa acagtatacagatgatggaattgttgtgtggagtgggaatgatgatcaat gtcatgatgctagatggggttatggggctaccggagtggtatctgttgcg agcaacctggttcccggtttaatgcgagaactcatgtttggcggtgtaaa ccctactctaaattctaaactcttgcctctgattgactggcttttccaca tgccaaacccatnggtttgaacactgctcttgctcaacttggggncatc
```

The above sequence was derived from the wild-type soybean sequence encoding the polypeptide of SEQ ID NO:4. The nucleotide sequence shown as SEQ ID NO:1 corresponds to sequences encoding the polypeptide of SEQ ID NO:5, a genetically altered AEC resistant DHPS sequence derived from soybean. The soybean DHPS sequence shown as SEQ ID NO:1 was modified from the wild-type to comprise a change of tgg to cgg at the indicated position in bold type. According to the invention, a soybean DHPS coding sequence comprising the indicated modification provides the desired AEC resistance.

The sequence was prepared using techniques well know to one skilled in the art. (e.g., Vauterin M, Frankard V, Jacobs M., Functional rescue of a bacterial dapA auxotroph with a plant cDNA library selects for mutant clones encoding a feedback-insensitive dihydrodipicolinate synthase, Plant J. February 2000; 21(3):239-48.; and Shaver, J., Bittel, D., Sellner, J., Frisch, D., Somers, D., Gengenbach, B. 1996 Single-amino acid substitutions eliminate lysine inhibition of maize dihydrodipicolinate synthase. *Proc. Natl Acad. Sci. USA*, 93, 1962 66).

It was shown in *Arabidopsis*, and populous deltoidsXpopulus tricho carpa modification of tryptophan53 (W) to Arginine53 (R) made the DHPS enzyme from these two plants insensitive to lysine concentrations up to 1 mM. *E. coli* auxotroph AT997 was rescued using these modified genes. This tryptophan residue is present in the consensus sequence MSWDEHI (SEQ ID NO: 6) in several plant DHPS genes (Vauterin et al.,2000). Clones expressing the insensitive plant DHPS enzymes were resistant to 2.5 mM 2-AEC. With our modified soybean DHPS gene we obtained similar results. We also targeted the tryptophan residue present in the consensus sequence MSWDEHI (SEQ ID NO: 6) in the soybean DHPS gene to convert it to arginine. With the modified gene we rescued the *E. coli* auxotroph AT998 and found that the rescued auxotroph grows well on minimal media plates with 0.5 mM 2-AEC concentrations. Native soybean DHPS gene failed to rescue the auxotroph while the modified soybean DHPS gene and native *E. coli* DHPS were successful in rescuing the mutant (data not shown).

Example 4

Method for Weed Control

The purpose of this example is to illustrate a method for weed control that has several potential advantages over existing methods.

Background:

The broadest class of major herbicides is the acetolactate synthase (ALS) inhibitors including the sulfonylureas, imidazolinones, sulfonamides and pyrimidinylthiobenzoate. DuPont and Syngenta have commercialized no less than 12 different sulfonylureas that target ALS. American Cyanamid (now BASF) have at least 6 different imidazolinones herbicides on the market all of which also target ALS (Shaner and O'Connor, 1991). ALS catalyzes the first step in the biosynthesis of the essential amino acids valine, isoleucine and leucine.

Via a mutagenesis program, DuPont has been able to produce an altered ALS in soybeans that is resistant to sulfonylureas and from this have developed sulfonylurea tolerant soybeans (STS) (Sebastian, 1990).

Roundup (glyphosate) also functions as an amino acid biosynthesis inhibitor targeting 5-enoylpyruvylshikimate 3-phosphate (EPSP) blocking aromatic amino acid biosynthesis.

All of these herbicides kill plants by starving them of essential amino acids but do not affect animals as essential amino acids in animals are obtained via their diets.

The selective agent AEC can be synthesized using N-(tert-butoxycarbonyl)serine and ethanolamine (Arnold et al., 1988). AEC is an inhibitor of dihydrodipicolinate synthase (DHPS) killing cells and tissues due to an inability to synthesize lysine (Perl et al., 1993; Ghislain et al., 1995; Vauterin et al., 2000). AEC also inhibits AK and lysine, which is also an inhibitor of DHPS (Negrutiu et al., 1984). AEC is shown below to be a more effective more effect herbicidal agent than lysine or lysine+threonine.

Results:

A major dicot and monocot weed of tobacco, pigweed (*Amaranthus retroflexus*) and giant foxtail (*Setaria faberi*) was used in addition to a model crop plant, tobacco. Initial experiments using 7 to 10 day old seedlings showed 10 mM lysine and threonine and above is lethal to pigweed, foxtail and tobacco. For larger plants grown in the green house 20 mM lysine and threonine or 40 mM lysine alone are needed for effective weed control. To increase uptake of these compounds, up to 0.2% Silwett (surfactant) was used. Silwett at 0.5% and above kills the plants. Silwett was not found to be a very effective surfactant. Studies with cultured cells and seedlings indicate that 100 µM levels of AEC are effective for selection.

Literature Cited

Each reference cited here is incorporated by reference as if each were individually incorporated by reference.

Arnold, L. D., R. G. May and J. C. Vederas. 1988. Synthesis of optically pure α-amino acids via salts of α-amino-β-propiolactone. J. Am. Chem. Soc. 110: 2237-2241.

Boy, E., Borne, F. and Patte, J. C. (1979). Isolation and identification of mutants constitutive for aspartate kinase III synthesis in *Escherichia coli* K12. Biochemie 61: 1151-1160.

Bright, S. W. J. and P. R. Shewry. 1983. Improvement of protein quality in cereals. CRC Crit. Rev. Plant Sci. 1: 49-93.

Cadogan, J. I. G., S. V. Ley, G. Pattenden, R. A. Raphael and C. W. Rees, eds. 1996. Dictionary of Organic Compounds, 6th edition. Chapman & Hall, London.

Cheng, Ming, et al, Methods for the production of stably transformed, fertile wheat employing *agrobacterium*-mediated transformation and compositions derived therefrom, U.S. Published Patent Application No. 20030024014

Cohen, C. N. and I Saint-Girons. 1987. Biosynthesis of threonine, lysine and methionine. In: F. C. Neidhardt, ed., *Escherichia coli* and *Salmonella typhimurium*: Cellular and Molecular Biology. Amer. Soc. Microbiol., Washington, D.C. pp 429-444.

Dey, P. M. and J. B. Harborne. 1997. Plant biochemistry. Academic Press, San Diego, Calif.

Ghislain, M., V. Frankard and M. Jacobs. 1995. A dinucleotide mutation in dihydrodipicolinate synthase of *Nicotiana sylvestris* leads to lysine overproduction. The Plant J. 8: 733-743.

Jacobs, M., Negrutiu, I., Dirks, R. and Cammaerts, D. (1987). Selection programs for isolation and analysis of mutants in plant cell cultures. In: Green C. E., Somers D. A., Hackett W. P. Biesboer D D (eds) Plant Biology. vol. 3: plant tissue and cell culture. Alan R. Liss, New York pp 243-264.

Perl A, Galili S, Shaul O, Ben-Tzvi I, Galili G (1993) Bacterial dihydrodipicolinate synthase and desensitized aspartate kinase: Two novel selectable markers for plant transformation. Bio Tech 11: 715-727.

Matsumoto, N. 1984. Isolation and identification of S-2-aminoethyl-L-systeine from *Rozites caperta* and 2-amino-3-butenoic acid from *Rhodophyllus crassipes* and their antibacterial activity. Toho Igakkai Zasshi 31: 249-264.

Negrutiu, I., A. Cattoir-Reynearts, I. Verbruggen and M. Jacobs. 1984. Lysine overproducer mutants with an altered dihydrodipicolinate synthase from protoplast culture of *Nicotiana sylvestris* (Spegazzini and Comes). Theor. Appl. Genet. 68: 11-20.

Sebastian, S. A. 1990. Soybean plants with dominant selectable trait for herbicide resistance. U.S. Pat. No. 5,084,082 assigned to E.I. Du Pont de Nemours and Company, Wilmington, Del.

Shaner, D. L. and S. L. O'Connor. 1991. The imidazolinone herbicides. CRC Press, Boca Raton, Fla.

Shaul, O. and Galili, G. (1992). Threonine overproduction in transgenic tobacco plants expressing a mutant desensitized aspartate kinase of *Escherichia coli*. Plant Physiology 100: 1157-1163.

Vauterin, M., V. Frankard and M. Jacobs. 2000. Functional rescue of a bacterial dapA auxotroph with a plant cDNA library selects for mutant clones encoding a feedback-insensitive dihydrodipicolinate synthase. The Plant J. 21: 239-248.

Report on the use of antibiotic resistance markers in genetically modified food organisms," advisory committee on novel foods and processes, July 1994.

Guenzi, Arron Charles, Selection for tolerance to s-2-aminoethylcysteine in wheat cell cultures, Ph.D. Dissertation, Kansas State University, 1989.

Falco S C, et al., Transgenic canola and soybean seeds with increased lysine, Biotechnology (NY) 13(6):577-82, 1995.

Shaul O, et al., Concerted regulation of lysine and threonine synthesis in tobacco plants expressing bacterial feedback-insensitive aspartate kinase and dihydrodipicolinate synthase, Plant Mol Biol; 23(4):759-68, 1993.

Brinch-Pedersen H, et al., Plant Mol Biol; 32(4):611-20, 1996).

We claim:

1. A method for generating a herbicide-resistant transgenic soybean plant comprising:

introducing into a soybean somatic embryogenic culture a DHPS-encoding polynucleotide comprising the sequence represented by SEQ ID NO: 1 and encoding a functional dihydrodipicolinate synthase (DHPS) polypeptide, operably linked to an expression control sequence, wherein DHPS expressed from the introduced DHPS-encoding polynucleotide is effective to render an embryo resistant to selection-effective amounts of S-2-aminoethylcysteine (2-AEC), and to render the plant resistant to herbicide-effective amounts of AEC, and contacting the embryo with selection effective amounts of 2-AEC.

2. The method of claim 1, wherein the expression-control sequence to which the DHPS-encoding polynucleotide is operably linked is a first expression control sequence.

3. The method of claim 2, further comprising introducing a polynucleotide encoding a heterologous polypeptide of interest, operably linked to a second expression control sequence wherein the first and second polynucleotides and their expression control sequences may be the same or different.

4. The method of claim 3, wherein the DHPS-encoding polynucleotide and/or the polypeptide of interest-encoding polynucleotide are stably integrated into the genome.

5. The method of claim 3, wherein the polynucleotide encoding the DHPS polypeptide and the polynucleotide encoding the polypeptide of interest are on the same molecule.

6. The method of claim 3, wherein the polynucleotide encoding the DHPS polypeptide, operably linked to the first expression control sequence, and the polynucleotide encoding the polypeptide of interest, operably linked to the second expression control sequence, are on separate molecules.

7. The method of claim 2, wherein the first expression control sequence is a constitutive promoter.

8. The method of claim 2, wherein the first expression control sequence comprises a cauliflower mosaic virus CaMV 35S promoter or a ribosomal RNA promoter.

9. The method of claim 3, wherein the second expression control sequence is a seed-specific promoter.

10. The method of claim 3, wherein the second expression control sequence comprises a glycinin, phaseolin, conglycinin, seed lectin, napin, zein or other seed-specific promoter.

11. The method of claim 2, wherein the sequence encoding the functional DHPS polypeptide is upstream of the sequence encoding the polypeptide of interest.

12. The method of claim 2, wherein the sequence encoding the functional DHPS polypeptide is downstream of the sequence encoding the polypeptide of interest.

13. The method of claim 3, wherein the heterologous polypeptide of interest is selected from the group consisting of omega-3 desaturase; a polypeptide for improved amino acid compositions; a polypeptide imparting resistance to a bacterium, a fungus, a virus, an insect, or a nematode; a herbicide resistance polypeptide; a polypeptide affecting soybean composition or quality; a nutrient utilization polypeptide; an environmental or stress resistance polypeptide; and a drought resistance polypeptide.

14. The method of claim 3, wherein the polypeptide of interest is phosphinothricin acetyltransferase, glyphosate resistant EPSPS, aminoglycoside phosphotransferase, dalapon dehalogenase, bromoxynil resistant nitrilase, anthranilate synthase and glyphosate oxidoreductase.

15. The method of claim 3, wherein the polypeptide of interest is a lysophosphatidate acyl transferase (LPAT).

16. The method of claim 3, wherein the polypeptide of interest is a diacylglycerol acyltransferase (DGAT).

17. The method of claim 3, wherein the polypeptide of interest provides increased oil content in the soybean.

18. The method of claim 3, wherein the polypeptide of interest is delta-9 desaturase.

19. The method of claim 18, wherein expression of the delta-9 desaturase activity results in a decreased saturated fatty acid contents in the soybean plant.

20. The method of claim 19, wherein the decreased fatty acid content results in palmitoleic acid accumulation in the soybean plant.

21. The method of claim 3, wherein the polypeptide of interest is delta-12 desaturase.

22. The method of claim 21, wherein expression of the delta-12 desaturase results in high oleic acid content soybean oil.

23. The method of claim 22, wherein the polypeptide of interest is a functional DHPS expressible in soybean plant and seed.

24. The method of claim 23, wherein the polypeptide of interest is the same as the DHPS-encoding sequence.

25. The method of claim 1, wherein a 3' terminator sequence is located 3'0 to the DHPS-encoding sequence.

26. The method of claim 25, wherein the 3' terminator sequence is a pea RUBISCO 3' controlling sequence, a ribosomal RNA terminator, or a 3' transcription region for the nopaline synthase (NOS) gene.

27. The method of claim 3, wherein one or both of the sequence encoding the functional DHPS polypeptide and the sequence encoding the heterologous polypeptide of interest is operably linked to two or more expression control sequences.

28. The method of claim 3, wherein the transgenic soybean plant is backcrossed so as to generate a transgenic soybean plant which is homozygous for the sequence encoding the heterologous polypeptide of interest.

29. The method of claim 1, further comprising backcrossing the transgenic soybean plant to generate a transgenic soybean plant which is homozygous for the sequence encoding the DHPS polypeptide.

30. The method of claim 1, wherein the transgenic plant is fertile.

31. The method of claim 1, wherein the embryo is contacted with a concentration of 2-AEC from about 0.1 to about 20 mM.

32. The method of claim 1, wherein the embryo is contacted with a concentration of 2-AEC from about 1 to about 2.5 mM.

* * * * *

```
                       SEQUENCE LISTING

<160> NUMBER OF SEQ ID NOS: 6

<210> SEQ ID NO 1
<211> LENGTH: 700
<212> TYPE: DNA
<213> ORGANISM: Glycine max
<220> FEATURE:
<221> NAME/KEY: MOD_RES
<222> LOCATION: (664)
<223> OTHER INFORMATION: a, c, g, t, unknown or other
<220> FEATURE:
<221> NAME/KEY: MOD_RES
<222> LOCATION: (696)
<223> OTHER INFORMATION: a, c, g, t, unknown or other

<400> SEQUENCE: 1
ctttggactc tgaagctatg atgacttggt gaatatgcag attggacaag gggctgaagg      60
tgttattgtt ggtgggacaa ctggtgaagg ccaattaatg agccgggaag agcacataat     120
acttattgct catacagtca actgtttttgg tgggaaaatt aaggttattg gaaatactgg    180
aagcaactcc accaggaag caattcatgc cactgagcag ggtttttgctg ttggaatgca     240 tgctgccctt cacataaacc cttactatgg caaaacctcc ttggatggta tggttgctca    300
ctttcgaagt gtgctttcca tgggacccac aataatctac aatgtgcctg cacggaccgg    360
acaagacatt cctccgcatg taattcaaac cttagctgaa agtgttaacc tggctggtgt    420
caaggagtgt gtgggaaatg accgaatcaa acagtataca gatgatggaa ttgttgtgtg    480
gagtgggaat gatgatcaat gtcatgatgc tagatggggt tatggggcta ccggagtggt    540
atctgttgcg agcaacctgg ttcccggttt aatgcgagaa ctcatgtttg gcggtgtaaa    600
ccctactcta aattctaaac tcttgcctct gattgactgg cttttccaca tgccaaaccc    660
catnggtttg aacactgctc ttgctcaact tggggncatc                          700
```

<210> SEQ ID NO 2
<211> LENGTH: 1197
<212> TYPE: DNA
<213> ORGANISM: Escherichia coli

<400> SEQUENCE: 2

```
ccaggcgact gtcttcaata ttacagccgc aactactgac atgacgggtg atggtgttca      60
caattccacg gcgatcggca cccaacgcag tgatcaccag ataatgtgtt gcgatgacag     120
tgtcaaactg gttattcctt aaggggtga gttgttctta aggaaagcat aaaaaaaaca     180
tgcatacaac aatcagaacg gttctgtctg cttgctttta atgccatacc aaacgtacca     240
ttgagacact tgtttgcaca gaggatggcc catgttcacg ggaagtattg tcgcgattgt     300
tactccgatg gatgaaaaag gtaatgtctg tcgggctagc ttgaaaaaac tgattgatta     360
tcatgtcgcc agcggtactt cggcgatcgt ttctgttggc accactggcg agtccgctac     420
cttaaatcat gacgaacatg ctgatgtggt gatgatgacg ctggatctgg ctgatgggcg     480
cattccggta attgccggga ccggcgctaa cgctactgcg gaagccatta gcctgacgca     540
gcgcttcaat gacagtggta tcgtcggctg cctgacggta accccttact acaatcgtcc     600
gtcgcaagaa ggtttgtatc agcatttcaa agccatcgct gagcatactg acctgccgca     660
aattctgtat aatgtgccgt cccgtactgg ctgcgatctg ctcccggaaa cggtgggccg     720
tctggcgaaa gtaaaaaata ttatcggaat caaagaggca acaggaact taacgcgtgt     780
aaaccagatc aaagagctgg tttcagatga ttttgttctg ctgagcggcg atgatgcgag     840
cgcgctggac ttcatgcaat tgggcggtca tggggttatt tccgttacga ctaacgtcgc     900
agcgcgtgat atgggcccaga tgtgcaaact ggcagcagaa gaacattttg ccgaggcacg     960
cgttattaat cagcgtctga tgccattaca aacaaacta tttgtcgaac ccaatccaat    1020
cccggtgaaa tgggcatgta aggaactggg tcttgtggcg accgatacgc tgcgcctgcc    1080
aatgacacca atcaccgaca gtggtcgtga cggtcaga gcggcgctta agcatgccgg    1140
tttgctgtaa agtttaggga gatttgatgg cttactctgt tcaaaagtcg cgcctgg      1197
```

<210> SEQ ID NO 3
<211> LENGTH: 292
<212> TYPE: PRT
<213> ORGANISM: Escherichia coli

<400> SEQUENCE: 3

```
Met Phe Thr Gly Ser Ile Val Ala Ile Val Thr Pro Met Asp Glu Lys
  1               5                  10                  15

Gly Asn Val Cys Arg Ala Ser Leu Lys Lys Leu Ile Asp Tyr His Val
             20                  25                  30

Ala Ser Gly Thr Ser Ala Ile Val Ser Val Gly Thr Thr Gly Glu Ser
         35                  40                  45

Ala Thr Leu Asn His Asp Glu His Ala Asp Val Val Met Met Thr Leu
     50                  55                  60

Asp Leu Ala Asp Gly Arg Ile Pro Val Ile Ala Gly Thr Gly Ala Asn
 65                  70                  75                  80

Ala Thr Ala Glu Ala Ile Ser Leu Thr Gln Arg Phe Asn Asp Ser Gly
                 85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125
```

```
Pro Gln Ile Leu Tyr Asn Val Pro Ser Arg Thr Gly Cys Asp Leu Leu
        130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
        195                 200                 205

Val Ala Ala Arg Asp Met Ala Gln Met Cys Lys Leu Ala Ala Glu Glu
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290

<210> SEQ ID NO 4
<211> LENGTH: 332
<212> TYPE: PRT
<213> ORGANISM: Glycine max

<400> SEQUENCE: 4

Met Ile Thr Asn Ser Ala Ala Val Lys Pro Asn Phe His Leu Pro Met
1               5                   10                  15

Arg Ser Phe Glu Leu Lys Asn Arg Thr Ser Pro Glu Asp Ile Lys Ala
            20                  25                  30

Leu Arg Leu Ile Thr Ala Ile Lys Thr Pro Tyr Leu Pro Asp Gly Arg
        35                  40                  45

Phe Asp Leu Glu Ala Tyr Asp Asp Leu Val Asn Met Gln Ile Gly Gln
    50                  55                  60

Gly Ala Glu Gly Val Ile Val Gly Gly Thr Thr Gly Glu Gly Gln Leu
65                  70                  75                  80

Met Ser Trp Glu Glu His Ile Ile Leu Ile Ala His Thr Val Asn Cys
                85                  90                  95

Phe Gly Gly Lys Ile Lys Val Ile Gly Asn Thr Gly Ser Asn Ser Thr
            100                 105                 110

Arg Glu Ala Ile His Ala Thr Glu Gln Gly Phe Ala Val Gly Met His
        115                 120                 125

Ala Ala Leu His Ile Asn Pro Tyr Tyr Gly Lys Thr Ser Leu Asp Gly
    130                 135                 140

Met Val Ala His Phe Arg Ser Val Leu Ser Met Gly Pro Thr Ile Ile
145                 150                 155                 160

Tyr Asn Val Pro Ala Arg Thr Gly Gln Asp Ile Pro Pro His Val Ile
                165                 170                 175

Gln Thr Leu Ala Glu Ser Val Asn Leu Ala Gly Val Lys Glu Cys Val
            180                 185                 190

Gly Asn Asp Arg Ile Lys Gln Tyr Thr Asp Asp Gly Ile Val Val Trp
        195                 200                 205
```

```
Ser Gly Asn Asp Asp Gln Cys His Asp Ala Arg Trp Gly Tyr Gly Ala
    210                 215                 220

Thr Gly Val Val Ser Val Ala Ser Asn Leu Val Pro Gly Leu Met Arg
225                 230                 235                 240

Glu Leu Met Phe Gly Gly Val Asn Pro Thr Leu Asn Ser Lys Leu Leu
                245                 250                 255

Pro Leu Ile Asp Trp Leu Phe His Met Pro Asn Pro Ile Gly Leu Asn
            260                 265                 270

Thr Ala Leu Ala Gln Leu Gly Val Ile Arg Pro Val Phe Arg Leu Pro
        275                 280                 285

Phe Val Pro Leu Pro Val Asp Lys Arg Ile Glu Phe Ala Asn Leu Val
290                 295                 300

Lys Glu Ile Gly Arg Glu His Phe Val Gly Asn Lys Val Val Glu Val
305                 310                 315                 320

Leu Asp Asp Asp Asp Phe Phe Leu Val Ser Arg Tyr
                325                 330

<210> SEQ ID NO 5
<211> LENGTH: 215
<212> TYPE: PRT
<213> ORGANISM: Glycine max

<400> SEQUENCE: 5

Tyr Asp Asp Leu Val Asn Met Gln Ile Gly Gln Gly Ala Glu Gly Val
  1               5                  10                  15

Ile Val Gly Gly Thr Thr Gly Glu Gly Gln Leu Met Ser Arg Glu Glu
                 20                  25                  30

His Ile Ile Leu Ile Ala His Thr Val Asn Cys Phe Gly Gly Lys Ile
             35                  40                  45

Lys Val Ile Gly Asn Thr Gly Ser Asn Ser Thr Arg Glu Ala Ile His
 50                  55                  60

Ala Thr Glu Gln Gly Phe Ala Val Gly Met His Ala Ala Leu His Ile
 65                  70                  75                  80

Asn Pro Tyr Tyr Gly Lys Thr Ser Leu Asp Gly Met Val Ala His Phe
                 85                  90                  95

Arg Ser Val Leu Ser Met Gly Pro Thr Ile Ile Tyr Asn Val Pro Ala
            100                 105                 110

Arg Thr Gly Gln Asp Ile Pro Pro His Val Ile Gln Thr Leu Ala Glu
        115                 120                 125

Ser Val Asn Leu Ala Gly Val Lys Glu Cys Val Gly Asn Asp Arg Ile
130                 135                 140

Lys Gln Tyr Thr Asp Asp Gly Ile Val Val Trp Ser Gly Asn Asp Asp
145                 150                 155                 160

Gln Cys His Asp Ala Arg Trp Gly Tyr Gly Ala Thr Gly Val Val Ser
                165                 170                 175

Val Ala Ser Asn Leu Val Pro Gly Leu Met Arg Glu Leu Met Phe Gly
            180                 185                 190

Gly Val Asn Pro Thr Leu Asn Ser Lys Leu Leu Pro Leu Ile Asp Trp
        195                 200                 205

Leu Phe His Met Pro Asn Pro
210                 215

<210> SEQ ID NO 6
<211> LENGTH: 7
<212> TYPE: PRT
```

-continued

```
<213> ORGANISM: Artificial Sequence
<220> FEATURE:
<223> OTHER INFORMATION: Description of Artificial Sequence: Synthetic
      consensus sequence

<400> SEQUENCE: 6

Met Ser Trp Asp Glu His Ile
1               5
```